United States Patent [19]
Senter

[11] Patent Number: 4,874,779
[45] Date of Patent: Oct. 17, 1989

[54] MITOMYCIN PHOSPHATE DERIVATIVES
[75] Inventor: Peter D. Senter, Seattle, Wash.
[73] Assignee: Bristol-Myers Company, New York, N.Y.
[21] Appl. No.: 213,201
[22] Filed: Jun. 29, 1988
[51] Int. Cl.$^4$ .................. C07D 487/14; A61K 31/40
[52] U.S. Cl. ................................. 514/410; 548/415; 548/422; 514/421
[58] Field of Search ............... 548/422, 415; 514/421, 514/410

[56] References Cited
U.S. PATENT DOCUMENTS
4,185,111 1/1980 Ducep et al. .................. 424/283
4,642,352 2/1987 Kaneko et al. .................. 548/422

OTHER PUBLICATIONS
Iyengar et al, J. Med. Chem., 1981, 24:975–981 and J. Med. Chem., 1983, 26:16–20.
Sinkula & Yalkowsky, J. Pharm. Sci., 1975, 64:181–210 at 189–191. Japan Kokai 21-95, 394 and 21-95, 393, Derwent Abst. No. 87-281016 and 87-281015.

Primary Examiner—Nicholas S. Rizzo
Attorney, Agent, or Firm—Mollie M. Yang

[57] ABSTRACT

Disclosed herein are $N^7$-alkylphosphate derivatives of mitomycin C and porfiromycin showing antitumor activity against transplanted human tumor and reduced toxicity relative to the parent $N^7$-alkanol mitomycin compounds.

9 Claims, 2 Drawing Sheets

MITOMYCIN PHOSPHATE DERIVATIVES

BACKGROUND OF THE INVENTION

1. Field of the Invention

The present invention relates to mitomycin $N^7$-alkyl phosphate derivatives, to their use as antitumor agents, and to pharmaceutical compositions containing them.

2. Background Art

Mitomycins and porfiromycin are a group of closely related antitumor antibiotics. Mitomycin C (Ia) is currently marketed in the United States under the tradename Mutamycin ® for therapy of disseminated adenocarcinoma of the stomach or pancreas in proven combinations with other approved chemotherapeutic agents. The structures of mitomycins C and A (Ib), porfiromycin (Ic), and $N^{1a}$-methyl mitomycin A (Id) are shown below with the numbering for the ring portion of the molecules. Throughout the specification

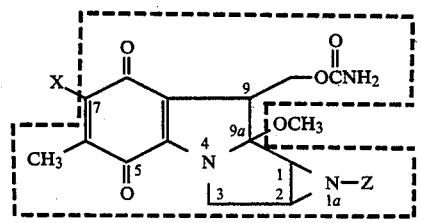

a: X = NH$_2$; Z = H
b: X = OCH$_3$; Z = H
c: X = NH$_2$; Z = CH$_3$
d: X = OCH$_3$; Z = CH$_3$ $N^7$- will refer to the nitrogen atom attached to the 7-position and $N^{1a}$- to the aziridine nitrogen. The portion enclosed within the dashed lines is referred to in the art as mitosane.

A large number of mitomycin analogs have been prepared with the object of finding a compound with more favorable therapeutic properties, such as higher antitumor activity and/or less myelosuppressive than mitomycin C. Among literature references and patents on mitomycin derivatives, the following are considered to be relevant to the present invention.

Iyengar et al disclose compounds IIa–IIc in J. Med. Chem., 1981, 24: 974–981 and J. Med. Chem., 1983, 26: 16–20.

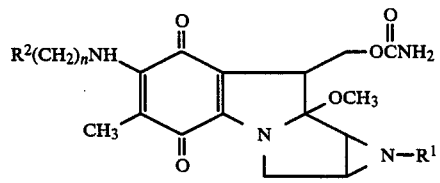

a: n = 2; R$^1$ = H; R$^2$ = OH
b: n = 3; R$^1$ = H; R$^2$ = OH
c: n = 3; R$^1$ = CH$_3$; R$^2$ = OH

Kaneko et al in U.S. Pat. No. 4,642,352 disclose mitomycin derivatives having the formula III

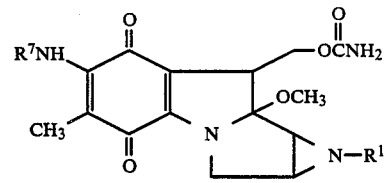

wherein $R^1$ is selected from H, $C_{1-6}$alkyl, and $R^7$, and $R^7$ is inter alia $(R^bO)_2P(X)$— and $(R^a)_2P(X)$— wherein $R^a$ is for example, H, alkyl, cycloalkyl, aryl; and $R^b$ is for example, alkyl, aryl, aralkyl.

Compounds of the present invention are phosphate derivatives of compounds of formula II; they show good antitumor activity and lower toxicity relative to the parent hydroxy compound. The concept of phosphates as potential prodrugs is briefly discussed in the review article entitled "Rational for Design of Biologically Reversible Drug Derivatives: Prodrugs" (Sinkula and Yalkowsky, J. Pharm. Sci., 1975, 64: 181–210 at 189–191). Examples of phosphates of known antitumor agents include camptothecin (Japan Kokai 21-95,394 and 21-95,393, Derwent Abst. No. 87-281016 and 87-281015, respectively) and daunorubicin (U.S. Pat. No. 4,185,111).

SUMMARY OF THE INVENTION

The present invention provides compounds of the formula IV

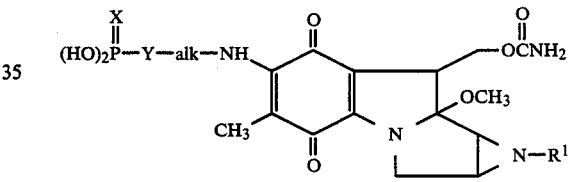

wherein X and Y are independently oxygen or sulfur; alk represents a linear or branched carbon chain having two to eight carbon atoms, and $R^1$ is H or methyl; or a pharmaceutically acceptable salt thereof. Pharmaceutically acceptable salts include, but are not limited to, alkali metal, alkaline earth metal, and organic nitrogen-containing base salts.

A preferred embodiment provides compounds of formula IV wherein Y is oxygen. Another preferred embodiment provides compounds of formula IV wherein alk is $(CH_2)_2$ or $(CH_2)_3$. Yet a further preferred embodiment provides compound of formula IV wherein $R^1$ is H.

DETAILED DESCRIPTION OF THE INVENTION

Compounds of the present invention are prepared from mitomycin A (Ib) or $N^{1a}$-methyl mitomycin A (Id) by reaction with an aminoalkyl phosphate of the formula $(HO)_2P(X)$—Y—alk—$NH_2$, wherein alk is as previously defined. The reaction is generally carried out in a suitable solvent such as methanol, or a mixture of solvents such as water and methanol, at ambient temperature. A tertiary amine base such as triethylamine may be included in the reaction mixture. The product may be converted into a salt by treatment with a base; thus, for example, treatment with sodium bicarbonate provides the disodium salt of mitomycin $N^7$-alkyl phosphates of formula IV. 2-Aminoethyl dihydrogen phosphate is a commercially available product and procedures for making other aminoalkylphosphates or ainoalkylthiophosphates may be found in, e.g., Helv. Chim. Act., 1956: 39: 1455; Helv. Chim. Acta, 1958, 44: 1168; Acta Chim. Scand., 1959, 13: 1479, and U.S. Pat. No. 3,501,557.

Alternatively, the compounds of the present invention may be prepared by treating mitomycin A or its $N^{1a}$-methylated derivative with an aminoalkanol or an aminoalkylthiol to provide $N^7$-hydroxyalkyl or $N^7$-thioalkyl mitomycin C intermediates which are subsequently phosphorylated or thiophosphorylated using conventional methods known in the art. This route, however, may not be suitable for making phosphate derivatives of $N^7$-mercaptoethyl mitomycin C as it is not a stable compound (Senter et al, 1988, J. Antibiotics, 41: 199–201). When mitomycin A is the starting material, it is desirable to protect the nitrogen of the aziridine ring before the phosphorylation reaction. Protection may be achieved by known procedures such as acylation, formation of urea or urethane derivatives, and the like. Methods of blocking and deblocking of an amine are discussed in textbooks such as "Protective Groups in Organic Chemistry" J. F. W. McOmie, Ed., Plenum Press, 1973. Phosphorylation or thiophosphorylation is typically done by treating a $N^7$-hydroxyalkyl or $N^7$-thioalkyl mitomycin derivative with phosphoryl or thiophosphoryl chloride followed by hydrolysis and de-protecting the aziridine nitrogen, if necessary; and if the hydrolysis is conducted in the presence of a base, the salt is obtained. Alternatively, the $N^7$-hydroxyalkyl or $N^7$-thioalkyl mitomycin derivatives may react with a compound of the formula $(G-O)_2P(X)-L$, wherein G is a phosphate protecting group and L is a leaving group, e.g. Cl; removal of the phosphate protecting group and the nitrogen protecting group, if present, provides compounds of the present invention.

BIOLOGICAL ACTIVITY

Figure 1:
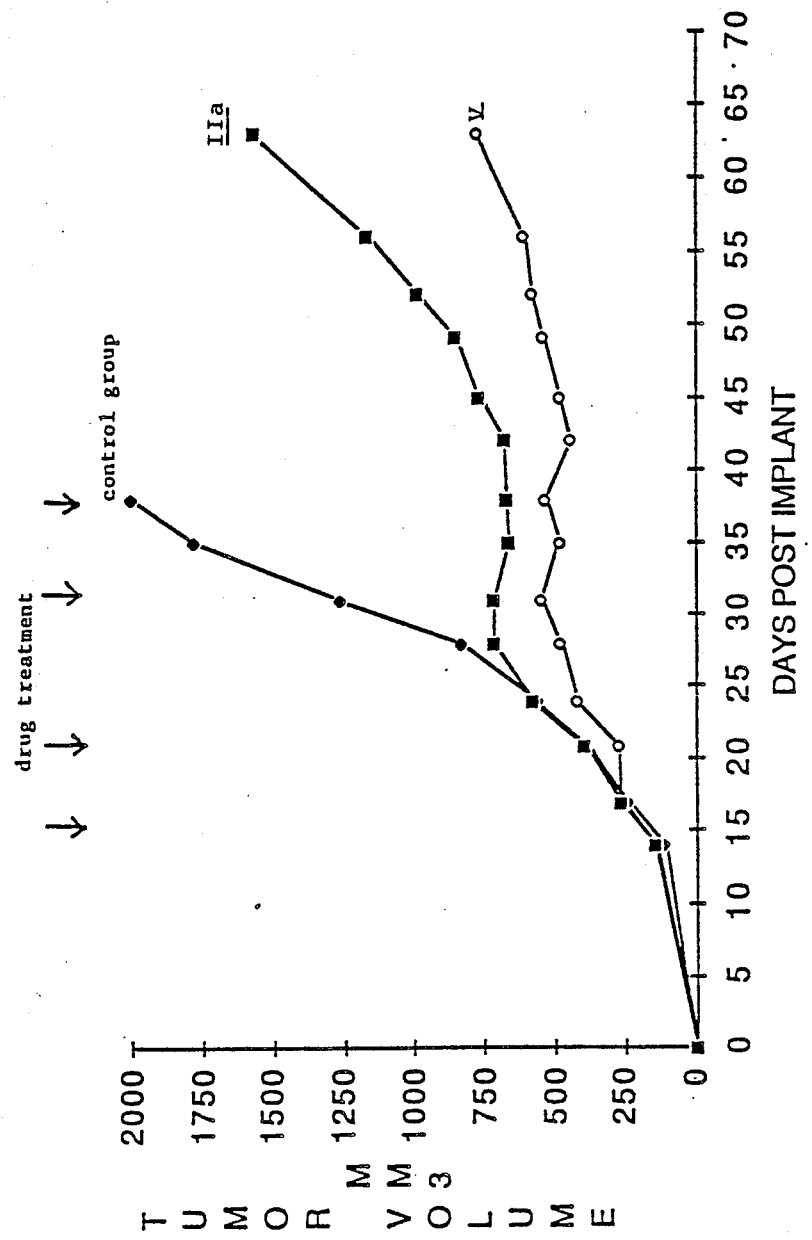
FIG. 1 shows the effect of compounds V and IIa on the growth of H2981 tumors in nude mice. The arrows indicate the days on which drugs were given.

Antitumor activity of the compound of Example 1 (V) was evaluated in Balb C nu/nu female mice (4–6 weeks old, purchased from Life Sciences, St. Petersburg, Fl) implanted subcutaneously with a xenograft of human lung tumor H2981 in the right hind flank. Compound IIa served as positive control. Drug treatment was initiated on day 15 (day 0 being the day of tumor implant) when the tumors were approximately 100 mm$^3$ in volume. 0.2 Ml of the test compounds (1 mg/ml for IIa and 3 mg/ml for V in phosphate-buffered saline) were injected intraperitoneally on days 15, 21, 31, and 37. The results are graphically shown in FIG. 1 and indicate that the time required to reach an average tumor volume of 750 mm$^3$ was 45 days in mice treated with IIa, 63 days in mice treated with V, and 27 days in the untreated control group. Thus, the phosphorylated compound displayed a stronger antitumor effect than the corresponding alcohol.

The relative toxicities of IIa and V were determined in Balb C nu/nu mice. When the drugs were administered intraperitoneally in two equal doses spaced 4 days apart, LD$_{50}$ values of 45 and 90 mg/kg body weight were obtained for IIa and V, respectively. It was also found that considerably more drug could be administered using smaller doses over a longer period of time. Total amounts of up to 40 mg/kg of IIa and 100 mg/kg of V were tolerated if given in 4 equal doses over a 25 day period. These studies indicated that significantly more prodrug was tolerated because of its reduced toxicity.

Figure 2:
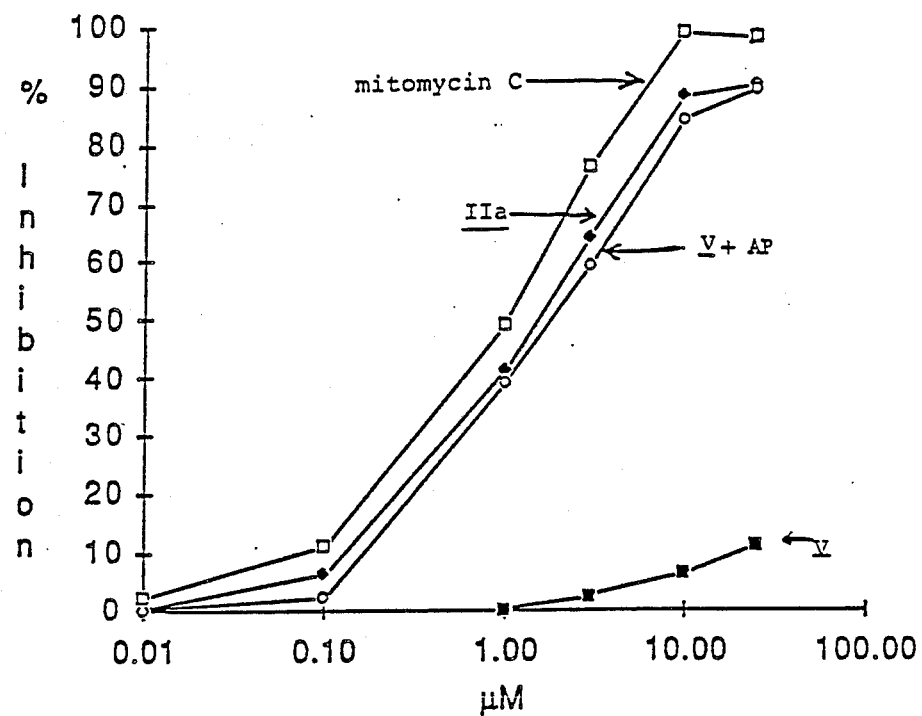
FIG. 2 shows cytotoxic effects of mitomycin C, compounds IIa and V, and compound V pretreated with alkaline phosphatase.

Cytotoxicity of compounds V, IIa, and mitomycin C was determined using human lung tumor cell line H2981. Thus a suspension of H2981 cells in Iscove's medium (IMDM) containing 10% fetal calf serum were plated into 96-well microtiter plates (10,000 cells/well). After 1 hr, the medium was removed, a pH 7.2 phosphate buffered saline solution (PBS) of the drug was added, and incubation at 37° C. was commenced for 1 hour. The cells were then washed twice, and incubation was continued an additional 17 hours, followed by a 6 hour pulse with $^3$H-Thy (1.0 $\mu$Ci/well). The plates were frozen at $-70°$ C. to detach the cells, and the cells were harvested onto glass fiber discs. The filters were counted on a Beckman 3701 scintillation counter. Inhibition of $^3$H-Thy incorporation was used as an indicator for cytotoxic effects. The results are shown in FIG. 2. Both mitomycin C and IIa were highly cytotoxic and had IC$_{50}$ values close to 1 $\mu$M. A small amount of cytotoxic activity was observed for the phosphate V, but pre-treatment of V with alkaline phosphatase resulted in cytotoxicity comparable to that of IIa and mitomycin C.

Thus another aspect of the present invention provides a method for inhibiting tumors which comprises administering an antitumor effective amount of a compound of formula IV to a tumor bearing host. For this purpose, the drug can be administered by conventional routes including, but are not limited to, intravenous, intramuscular, intratumoral, intraarterial, intralymphatic, and oral. Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

A further aspect of the present invention provides a pharmaceutical composition which comprises a compound of formula IV and a pharmaceutically acceptable carrier. The antitumor composition may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

The following examples are for illustrative purposes only and should not be construed as limiting the scope of the invention which is defined solely by the claims appended to this application.

EXAMPLE 1

9a-Methoxy-7-[[(phosphonooxy)ethyl]amino]mitosane disodium salt (V)

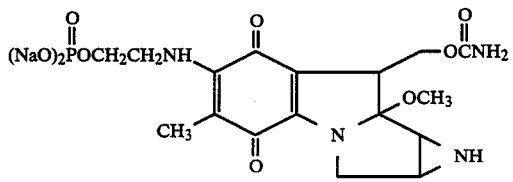

A solution of 2-aminoethyl dihydrogen phosphate (56 mg, 0.4 mmol) in water (0.35 ml) and triethylamine (0.3 ml, 2 mmol) was added to mitomycin A (140 mg, 0.4 mmol) in methanol (6 ml). The reaction was allowed to proceed at room temperature overnight, 1.4 ml of saturated aqueous sodium bicarbonate was added, and the solution was partitioned between water and methylene chloride. The aqueous phase was concentrated to dryness, and several portions of methanol were added and evaporated. The residue was taken up into methanol, filtered, and applied to a 2×10 cm C-18 (reverse phase) silica column. The product was eluted with water, and all volatile material was evaporated. Methanol was added and evaporated as before, and the residue was dried for 24 hours under high vacuum in a desiccator with phosphorus pentoxide. The title compound was obtained as a fine blue powder (190 mg, 97%).

360 MHz $^1$H-NMR (D$_2$O) δ 1.94 (s, 3H, CH$_3$), 2.9–3.1 (m, 4H), 3.20 (s, 3H, OCH$_3$), 3.28 (s, 1H), 3.36 (s, 1H), 3.5–3.65 (m, 4H), 4.1–4.25 (m, 2H), 4.50–4.57 (dd, 1H, 10-H).

Mass spectrum M+ 503.0912 (calculated from C$_{17}$H$_{21}$N$_4$O$_9$PNa$_2$ 503.0920).

EXAMPLE 2

The general procedure of Example 1 is repeated using N$^{1a}$-methyl mitomycin A instead of mitomycin A to provide 9a-methoxy-1a-methyl-7-[[(phosphonooxy)ethyl]amino]mitosane disodium salt.

EXAMPLE 3

The general procedure of Example 1 is repeated using 2-aminoethyl dihydrogen thiophosphate instead of 2-aminoethyl dihydrogen phosphate to provide 9a-methoxy-7-[[(phosphonothio)ethyl]amino]mitosane disodium salt.

I claim:

1. A compound having the formula

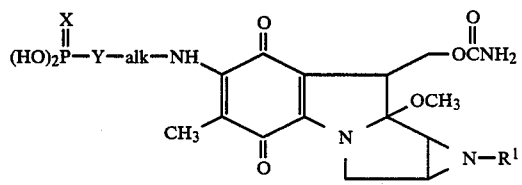

wherein
X and Y are independently oxygen or sulfur;
alk represents a linear or branched carbon chain having 2 to 8 carbon atoms; and
R$^1$ is H or methyl;
or a pharmaceutically acceptable salt thereof.

2. The compound of claim 1 wherein Y is oxygen.
3. The compound of claim 1 wherein R$^1$ is H.
4. The compound of claim 1 wherein alk is (CH$_2$)$_2$ or (CH$_2$)$_3$.
5. The compound of claim 1 wherein the pharmaceutically acceptable salt is the sodium salt.
6. The compound of claim 1 having the formula

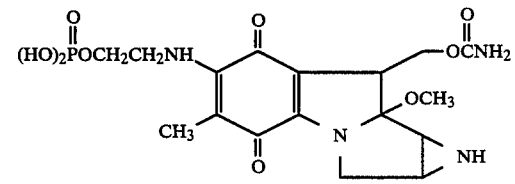

or a pharmaceutically acceptable salt thereof.

7. The disodium salt of said compound of claim 6.
8. A method of inhibiting tumor growth in a mammalian host which comprises administering to said host a tumor-inhibiting amount of a compound of claim 1.
9. A pharmaceutical composition which comprises a tumor-inhibiting amount of a compound of claim 1 and a pharmaceutically acceptable carrier.

* * * * *